(12) United States Patent
Myrick et al.

(10) Patent No.: US 8,902,423 B2
(45) Date of Patent: Dec. 2, 2014

(54) CLASSIFICATION USING MULTIVARIATE OPTICAL COMPUTING

(71) Applicant: University of South Carolina, Columbia, SC (US)

(72) Inventors: Michael L. Myrick, Columbia, SC (US); Timothy J. Shaw, Columbia, SC (US); Tammi L. Richardson, Columbia, SC (US); Laura S. Bruckman, Cleveland Heights, OH (US); Megan R. Pearl, Columbia, SC (US); Joseph A. Swanstrom, Lexington, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 13/683,589

(22) Filed: Nov. 21, 2012

(65) Prior Publication Data

US 2013/0162999 A1 Jun. 27, 2013

Related U.S. Application Data

(60) Provisional application No. 61/563,201, filed on Nov. 23, 2011.

(51) Int. Cl.
*G01J 3/28* (2006.01)
*G01J 3/44* (2006.01)
*G01N 21/31* (2006.01)
*G01N 21/64* (2006.01)

(52) U.S. Cl.
CPC ............ *G01J 3/4406* (2013.01); *G01J 3/28* (2013.01); *G01N 21/31* (2013.01); *G01N 21/6486* (2013.01)
USPC .......................................... 356/319; 356/326

(58) Field of Classification Search
CPC ...... G01J 3/28; G01J 3/4406; G01N 21/6488; G01N 21/31
USPC ................ 356/319, 326, 416, 402; 250/459.1
See application file for complete search history.

(56) References Cited

U.S. PATENT DOCUMENTS

| | | | |
|---|---|---|---|
| 6,198,531 B1 | 3/2001 | Myrick et al. | |
| 6,529,276 B1 | 3/2003 | Myrick et al. | |
| 6,723,516 B1 * | 4/2004 | Tom-Moy et al. | 435/7.1 |
| 6,864,978 B1 * | 3/2005 | Hazen et al. | 356/326 |
| 7,697,141 B2 * | 4/2010 | Jones et al. | 356/445 |
| 7,834,999 B2 * | 11/2010 | Myrick et al. | 356/303 |
| 7,899,636 B2 * | 3/2011 | Bakker | 702/85 |
| 7,911,605 B2 | 3/2011 | Myrick et al. | |
| 7,920,258 B2 | 4/2011 | Myrick et al. | |
| 7,990,538 B2 | 8/2011 | Myrick et al. | |
| 8,208,147 B2 | 6/2012 | Myrick et al. | |
| 8,213,006 B2 | 7/2012 | Myrick et al. | |
| 8,240,189 B2 * | 8/2012 | Myrick et al. | 73/24.02 |
| 2009/0268203 A1 * | 10/2009 | Uzunbajakava et al. | 356/436 |

\* cited by examiner

*Primary Examiner* — Sang Nguyen
(74) *Attorney, Agent, or Firm* — Dority & Manning, P.A.

(57) ABSTRACT

Methods for in situ detection and classification of analyte within a fluid sample are provided. In one embodiment, the method can include: (a) continuously flowing the fluid sample through a multivariate optical computing device, wherein the multivariate optical computing device illuminates an area of the fluid sample as it flows through the multivariate optical computing device to elicit a continuous series of spectral responses; (b) continuously measuring the series of multivariate spectral responses as the fluid sample flows through the multivariate optical computing device; (c) detecting an analyte (e.g., phytoplankton) in the sample based on an multivariate spectral response of the plurality of spectral responses; and (d) classifying the analyte based on the multivariate spectral response generated by the analyte.

13 Claims, 13 Drawing Sheets

CLASSIFICATION USING MULTIVARIATE OPTICAL COMPUTING

PRIORITY INFORMATION

The present application claims priority to U.S. Provisional Patent Application Ser. No. 61/563,201 titled "Classification Using Multivariate Optical Computing" of Myrick, et al. filed on Nov. 23, 2011, the disclosure of which is incorporated herein by reference.

GOVERNMENT SUPPORT CLAUSE

This invention was made with government support under contract number (OCE0623400) awarded by NSF's Division of Ocean Technology and Interdisciplinary Coordination. The government has certain rights in the invention.

BACKGROUND

Plankton are any drifting organisms, animals, plants, archaea, or bacteria, that inhabit the pelagic zone, water not close to the bottom or shore, of oceans, seas, or bodies of fresh water. Plankton are defined primarily by their ecological niche rather than phylogenetic or taxonomic classification. They provide a crucial source of food to larger, more familiar aquatic organisms such as fish and cetacea.

Types of plankton include: phytoplankton, which are autotrophic, prokaryotic or eukaryotic algae that live near the water surface where there is sufficient light to support photosynthesis; zooplankton, which are small protozoans or metazoans (e.g. crustaceans and other animals) that feed on other plankton; and bacterioplankton, bacteria and archaea, which play an important role in remineralising organic material down the water column, a conceptual column of water from surface to bottom sediments used chiefly for environmental studies evaluating the stratification or mixing (e.g. by wind induced currents) of the thermal or chemically stratified layers in a lake, stream or ocean. Some of the common parameters analyzed in the water column are: pH, turbidity, temperature, salinity, total dissolved solids, various pesticides, pathogens and a wide variety of chemicals and biota.

Phytoplankton, also known as microalgae, are similar to terrestrial plants in that they contain chlorophyll and require sunlight in order to live and grow. Most phytoplankton are buoyant and float in the upper part of the ocean, where sunlight penetrates the water. Phytoplankton are the foundation of the aquatic food web, the primary producers, feeding everything from microscopic, animal-like zooplankton to multi-ton whales. When too many nutrients are available, phytoplankton may grow out of control and form harmful algal blooms. These blooms can produce extremely toxic compounds that have harmful effects on marine, fowl, and mammals, including humans.

Phytoplankton growth depends on the availability of carbon dioxide, sunlight, and nutrients. Phytoplankton, like land plants, require nutrients such as nitrate, phosphate, silicate, and calcium at various levels depending on the species. Some phytoplankton can fix nitrogen and can grow in areas where nitrate concentrations are low. They also require trace amounts of iron which limits phytoplankton growth in large areas of the ocean because iron concentrations are very low. Other factors influence phytoplankton growth rates, including water temperature and salinity, water depth, wind, and what kinds of predators are grazing on them.

Knowledge of phytoplankton size and taxonomic composition is critical to characterizing biogeochemical cycles and quantifying carbon export. It is essential for predicting the ocean's response to future climate change. Shifts in species size or taxonomic composition, for example, may affect zooplankton grazing, and the packaging of material into fecal pellets, which will in turn impact carbon export from, or recycling within, the water column. As phytoplankton community structure, i.e., the various species and types of phytoplankton in the area, can be highly variable in space and time, its characterization requires sensors that can monitor continuously, and be deployed at multiple fixed locations or used on tethered or autonomous underwater vehicles (AUVs).

The need for in situ sensors has received increasing recognition by the oceanographic community in the past few years. Programs such as ORION/OOI and NOPP have enhanced scientific ocean observing capabilities, both in near-shore and open-ocean environments. While most ocean sensing platforms are equipped with a fluorometric sensor for chlorophyll a (chl a), this pigment (or a derivative) is found in all microalgae and thus cannot be used to discriminate between different phytoplankton taxa or to discern cell size.

Significant progress has been made on the development of in situ, i.e., on site, flow cytometric instruments that are capable of automated characterization of phytoplankton communities, however these instruments requiring cabling to a shore-based observatory. Satellite-based ocean color sensors provide critical information on phytoplankton biomass across broad swaths of the sea but characterization of community composition by satellite is difficult and generally limited to species with unique optical signatures.

A trend appears to be emerging toward in situ instruments capable of obtaining greater detail in both phytoplankton morphology and spectroscopy. Bulk optical spectroscopy measurements suffer from overlap of the spectra of many taxa. Mathematical methods exist to separate limited numbers of different fluorescent species from one another. However, the most general and accepted approach to disentangling the optical spectra of differing phytoplankton is to isolate them for individual measurement, either by cytometry or by imaging.

Flow cytometry on naturally-occurring phytoplankton provides both light scattering (size-related information) and laser-excited fluorescence emission intensity (pigment-related information). Light scattering is linked by theory to the morphology and optical constants of phytoplankton, although the mathematics cannot be inverted to determine exact morphology from light scattering. The fluorescence measured by a flow cytometer from natural phytoplankton is likewise limited because not enough of the excitation spectrum of the pigments is usually sampled. Many of the currently-available spectral fluorescence-based instruments, such as the Mini-Tracka II (Chelsea Instruments, UK), the Algae Online Monitor (Photon Systems Instruments, Czech Republic) and the Algae Online Analyzer (bbe Moldaenke, Germany; Beutler et al. 2002) suffer from poor discrimination abilities due to the limited number of excitation wavelengths.

Imaging provides more information about size and shape than light scattering can provide. Many reports on flow cytometry also provide details of microscopic analysis as a standard for comparison. In one embodiment, flow cytometry may be augmented with rapid imaging if the intention is to obtain information on dominant species. Conversely, fast automated imaging alone has not been shown to discriminate among a wide range of phytoplankton and other particles. Imaging may be coupled with fluorescence for the purpose of classifying or identifying plankton. Full-spectrum absorption spectroscopy has been shown to be a useful tool for classification. However, this technique does not give phytoplankton size and gives relatively limited information on phytoplankton community composition.

Sensors that can be deployed broadly on mobile or fixed platforms that give detailed information on phytoplankton size and species composition have remained elusive. What is needed is a new instrument for in situ discrimination of phytoplankton size and community composition that is compact, inexpensive, and has low power requirements.

SUMMARY

Objects and advantages of the invention will be set forth in part in the following description, or may be obvious from the description, or may be learned through practice of the invention.

Methods are generally provided for in situ detection and classification of analyte within a fluid sample. In one embodiment, the method can include: (a) continuously flowing the fluid sample through a multivariate optical computing device, wherein the multivariate optical computing device illuminates an area of the fluid sample as it flows through the multivariate optical computing device to elicit a continuous series of spectral responses; (b) continuously measuring the series of multivariate spectral responses as the fluid sample flows through the multivariate optical computing device; (c) detecting an analyte (e.g., phytoplankton) in the sample based on an multivariate spectral response of the plurality of spectral responses; and (d) classifying the analyte based on the multivariate spectral response generated by the analyte.

For example, continuously measuring the series of multivariate spectral responses as the fluid sample flows through the multivariate optical computing device can be achieved by continuously recording the series of multivariate spectral responses as the fluid sample flows through the multivariate optical computing device, wherein each multivariate spectral response is formed from a combination of a plurality of excitation spectra, each filtered by a multivariate optical element having a different transmission curve.

In one embodiment, the multivariate spectral response is formed by illuminating the analyte with a beam of light to excite the electrons in molecules of the analyte causing them to emit light of a lower energy. For instance, the beam of light can be filtered prior to exciting the electrons in molecules of the analyte. Additionally, the beam of light can pass through at least two multivariate optical elements to excite the electrons in molecules of the analyte, wherein the spectra response formed by excitation of each filter is combined to form the multivariate spectral response. For example, each filter can have a multi-wavelength spectral transmission curve that is different than the other filter.

When utilized as a method of in situ detection and classification of the species of phytoplankton within a water sample, the water sample can be pumped from a natural body of water (e.g., a lake or ocean).

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

DETAILED DESCRIPTION

Figure 1:
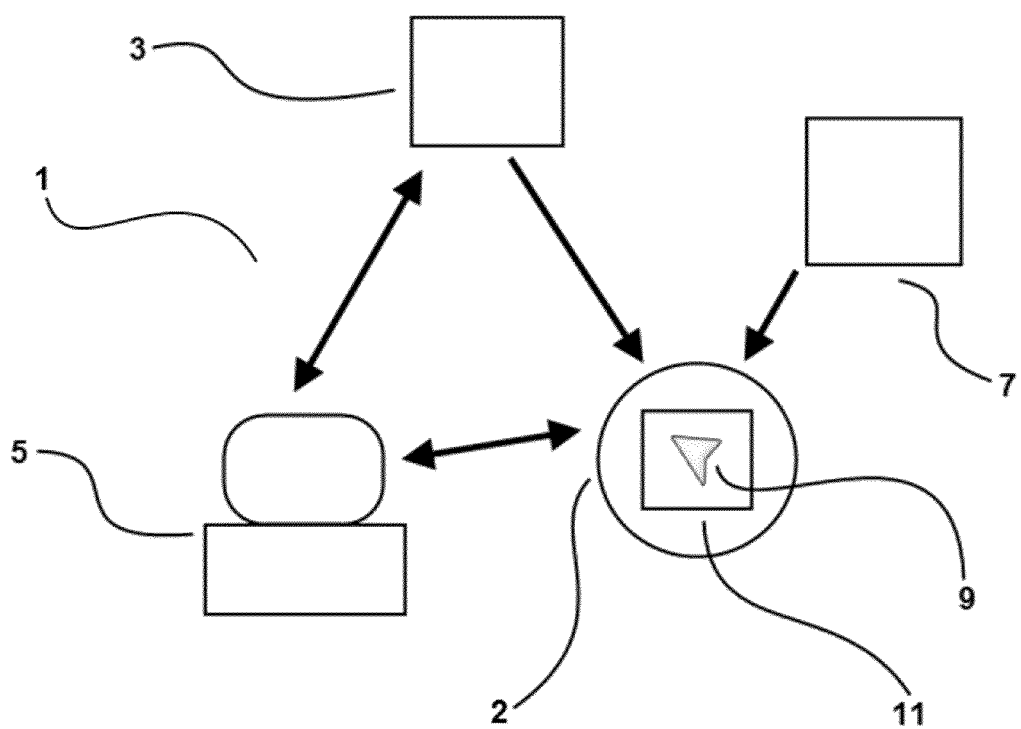
FIG. 1 shows a system that may be used to calibrate MOE data for constructing MOE filters.

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

For purposes of example only and not intended to be limiting, the present disclosure is generally directed toward a new instrument for in situ discrimination of analyte detection including but not limited to phytoplankton size and community composition. In other embodiments, the disclosure may be used to monitor fluorescent particles such as fluorescent beads used in biomedical sensing, bacteria labeled with fluorescent tags, or freshwater plankton such as algae. One embodiment is an instrument that may be compact, inexpensive and require low power. The instrument may be a multivariate optical computing based instrument and could complement existing chlorophyll fluorescence sensors by discriminating between functionally-distinct taxa, and may aid in data-product validation in support of present or future satellite-based taxon-specific ocean color measurements.

The current disclosure is generally based on the principle of spectral excitation fluorescence, a type of electromagnetic spectroscopy which analyzes fluorescence from a sample that involves using a beam of light to excite the electrons in molecules of certain compounds and cause them to emit light of a lower energy, combined with multivariate discrimination of spectral components, a method for compressing a multivariate signal to yield a lower dimensional signal amenable to classification.

Identification of analytes, for instance phytoplankton, based on spectral fluorescence provides an alternative to imaging flow cytometric analysis that is well-suited to continuous monitoring. Spectral fluorescence can discriminate phytoplankton based on the differing composition of antenna and accessory pigments between taxonomic groups of algae. All photosynthetic organisms contain chlorophyll a (or a derivative thereof) and most algal groups contain one of the accessory chlorophylls, chl b or chl c, along with a complement of photosynthetic and photoprotective carotenoids that vary widely in structure between classes, but whose main function is to absorb wavelengths of light not absorbed by the chlorophylls (e.g. fucoxanthin in diatoms). The phycobilins (phycocyanin and phycoerythrin) are accessory pigments found in rhodophytes, cyanobacteria, and cryptophytes that also absorb in the region where the chlorophylls do not. The excitation of different pigments by light of varying wavelengths, therefore, may result in characteristic fluorescence excitation spectra for the major algal groups. Thus, the use of spectral fluorescence to distinguish between algal groups utilizes the degree of dissimilarity of their characteristic pigment complements.

When using spectral fluorescence to distinguish between taxa of phytoplankton, one must be wary of within-taxon changes in pigment complements that result from variations in nutrient and light history of the organism. A common response to nutrient limitation and starvation, for example, is that the ratio of carotenoids to chlorophylls rises. This occurs when either Nitrogen or Phosphorous is the limiting nutrient. Physiological shifts in pigment composition have also been observed in Fe-stressed diatoms, raphidophytes, and prymnesiophytes. In most cases, Fe limitation depresses chlorophyll a more than accessory pigments. Changes in the absolute and relative concentrations of photopigments will manifest as changes in the fluorescence excitation spectra. Thus, while fluorescence excitation spectroscopy provides some discrimination between taxa, the variability of composition with growth conditions complicates the effort. Discrimination by in situ fluorescence excitation spectroscopy may be improved with knowledge of how the pigment composition depends on the broad range of light and nutrient conditions. Therefore, it is necessary to culture representative organisms under a range of these variables to characterize the resulting spectral changes. This may allow finding discriminant functions that are independent of the spectral changes due to growth conditions.

At least two classes of optical tools may be used for measurements: photometers and spectrometers. The former is simpler—a simple optical bandpass filter placed in front of a detector or camera. Unfortunately, complex spectroscopic problems, for example discrimination of phytoplankton taxa based on their fluorescence excitation spectra, are beyond the range of photometer-type instruments because they cannot acquire full spectrum information. Spectrometers are more complex and less rugged than photometers, and they are often bulky and expensive. However, they provide full spectrum capability, invaluable in many measurements because mathematical tools exist to recognize and measure patterns of intensity across a full spectrum. Use of these patterns can provide answers to the more sophisticated questions that photometers cannot address.

Multivariate optical computing (MOC) is a technique that combines the advantages of common photometers with the power of full-spectrum calibration. MOC depends on the design of special optical interference filters called multivariate optical elements (MOEs) whose design is performed by iterative refinement. Like conventional linear discriminant analysis (LDA), the design of these MOEs is based on models of training data. Unlike conventional LDA, the result of MOE modeling is an optical filter that can be used to project new optical spectra onto a discriminant function without needing a spectrometer.

MOC, or imaging multivariate optical computing (IMOC), uses fluorescence excitation spectral information to label or "bar code" different phytoplankton taxa by optical discriminant analysis. Multivariate optical computing is a predictive spectroscopy technique that incorporates a multi-wavelength spectral weighting directly into analytical instrumentation, and is generally described in U.S. Pat. No. 7,911,605 to Myrick et al.; U.S. Pat. No. 6,198,531 B1 to Myrick et al.; U.S. Pat. No. 6,529,276 B1 to Myrick; U.S. Pat. No. 8,208,147 to Myrick et al.; U.S. Pat. No. 8,213,006 to Myrick et al.; U.S. Pat. No. 7,990,538 to Myrick, et al.; U.S. Pat. No. 7,920,258 to Myrick et al., all of which are incorporated herein for all purposes by reference thereto. This technique is in contrast to traditional data collection routines where digitized spectral data is post-processed with a computer to correlate spectral signal with analyte concentration.

MOC can simplify the instrumentation and data analysis requirements of a traditional multivariate calibration. Specifically, the MOE utilizes a thin film interference filter to sense the magnitude of a spectral pattern. A no-moving parts spectrometer highly selective to a particular analyte may be constructed by designing simple calculations based on the filter transmission and reflection spectra. Other possible ways of performing optical computations include the use of weighted integration intervals and acousto-optical tunable filters, digital mirror arrays and holographic gratings.

A phenomenon in MOC has been identified and designated as the MOC passband disadvantage that has been defined as the cost of including large spectral windows in which the sample shows no absorbance. The phenomenon is analogous to the multiplex disadvantage sometimes observed in FT-Raman spectroscopy of weak bands in the presence of stronger features. The passband disadvantage increases noise in a measurement without improving, and sometimes harming, the ability to chemometrically model a chemical system.

The MOC passband disadvantage, like the FT Raman multiplex disadvantages, as known to those of skill in the art, like not completely eliminating fluorescence background, may be addressed by restricting the spectral band of a measuring device to wavelengths of greatest interest using physical optics means like filtering or by using special light sources, etc.

Many of the best and most convenient methods for physical wavelength selection have undesirable consequences such as irreproducibility. Interference filters, for instance, vary from production lot to production lot, and can even vary within a single lot. For this reason, the physical properties of bulk materials have generally been relied on to provide the most stable wavelength selection. This same phenomenon affects the reproducibility of simple bandpass photometers, where the filtering elements vary from instrument to instrument, making calibrations instrument-dependent.

In one embodiment herein, a more ideal selection of wavelengths may be made by using detectors whose wavelength response is tuned more directly and reproducibly toward the spectral intensity of the analyte whose measurement is sought. The response better correlates with analyte concentration in mixtures than would those of a broadband detector, even in the absence of any additional treatment. This is believed to improve the consistency of photometers and, if used in a MOC system, may provide enhanced performance and reduced sensitivity to spectral interferences.

In one embodiment, the MOC technique may require creating interference filters, one mimicking each linear discriminant function required for classification of different phytoplankton taxa. Thus, the design of MOEs may be based on LDA training data. Referring to FIG. 1, one embodiment of a system to calibrate MOE data for constructing filters is illustrated. As shown in FIG. 1, a calibration system 1 is shown. It includes a microscope 2, which may be a an inverted epifluoresence microscope (available from Nikon), that is coupled to a laser 3, which may be an infrared lasers that emits single or multiple beams, a computer 5, an illumination source 7, a dichroic beam splitter 13, an avalanche photodiode 15, and a spectrometer 17, which may be a single cell spectral fluorometer. Laser 3 functions as "optical tweezers" that trap analyte 9 in microscope viewing area 11. Optical tweezers or a "single-beam gradient force trap" are scientific instruments that use a highly focused laser beam to provide an attractive or repulsive force (typically on the order of piconewtons), depending on the refractive index mismatch to physically hold and move microscopic dielectric objects. This optical trap allows for obtaining reproducible fluorescence measurements. This, in turn, allows for analyzing different analytes, including but not limited to species of plankton, by optical discriminant analysis. Fluorescence is collected through the exciting objective via a dichroic beamsplitter 13. Calibrated excitation spectra are acquired using a spectrometer 17, preferably with a 150 W Xenon arc excitation source in order to determine the absolute spectral irradiance of the phytoplankton in all wavelengths. Fluorescence is coupled back out to an avalanche photodiode 15. The photodiode may be equipped with a chl a fluorescence emission filter, not shown, to provide the best signal-to-noise. In one embodiment, one filter is required for each discriminant function. In a further embodiment, multiple filters may be required. In a still further embodiment, MOEs may be designed by iterative refinement as known to those of skill in the art. Other potential calibrations that may be used include full-size fluorometers such as non-microscope based or employ fluorescence spectra of reporter dyes in a bacterium or pathogen detection scheme.

Figure 2:
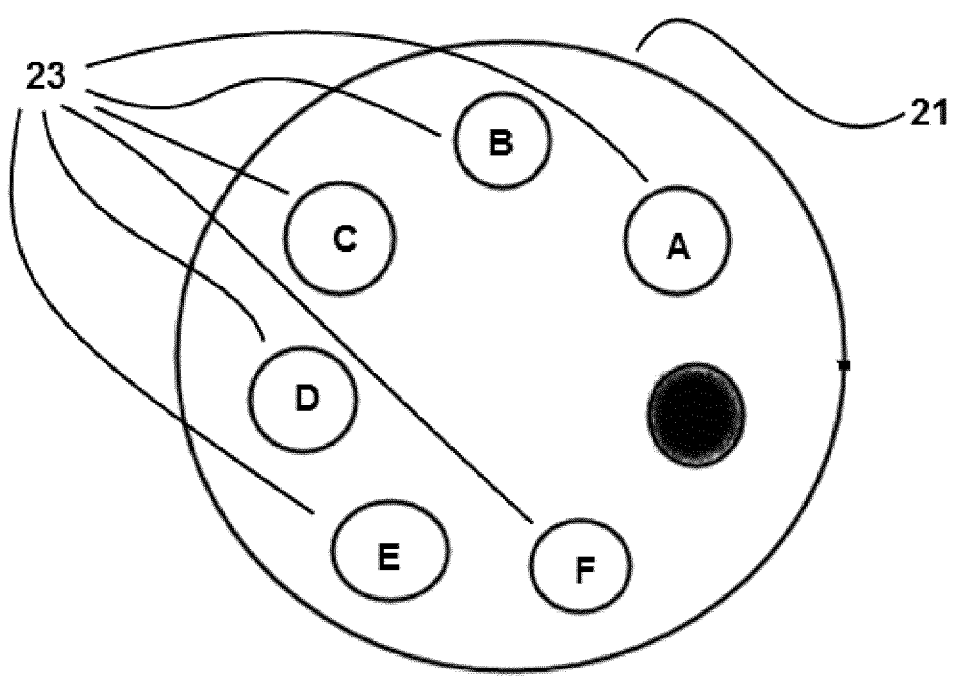
FIG. 2 is a plan view of a filter wheel for containing MOEs.

Referring now to FIG. 2, a filter wheel 21 for containing MOEs is illustrated. Filter wheel 21 includes MOE filters 23. MOE Filters 23 may encode discriminant functions A-F in their transmission spectra. While six MOE filters are currently shown in the illustrated embodiment of FIG. 2, this is not intended to be limiting as more or less filters may be used (e.g., at least two filters, such as about 3 to about 10 filters). Moreover, MOE filters 23, while shown containing a single discriminant factor may contain one or more discriminant factors or multiple MOE filters may be affixed overtop one another to a single spot on filter wheel 21. In further embodiments, multiple filter wheels 21 may be aligned with one another.

MOE filters 23 are placed in filter wheel 21 and target analytes, such as for purposes of example only, phytoplankton, are excited by spinning the series of filters, producing a classifying "bar code" in the image.

Figure 3:
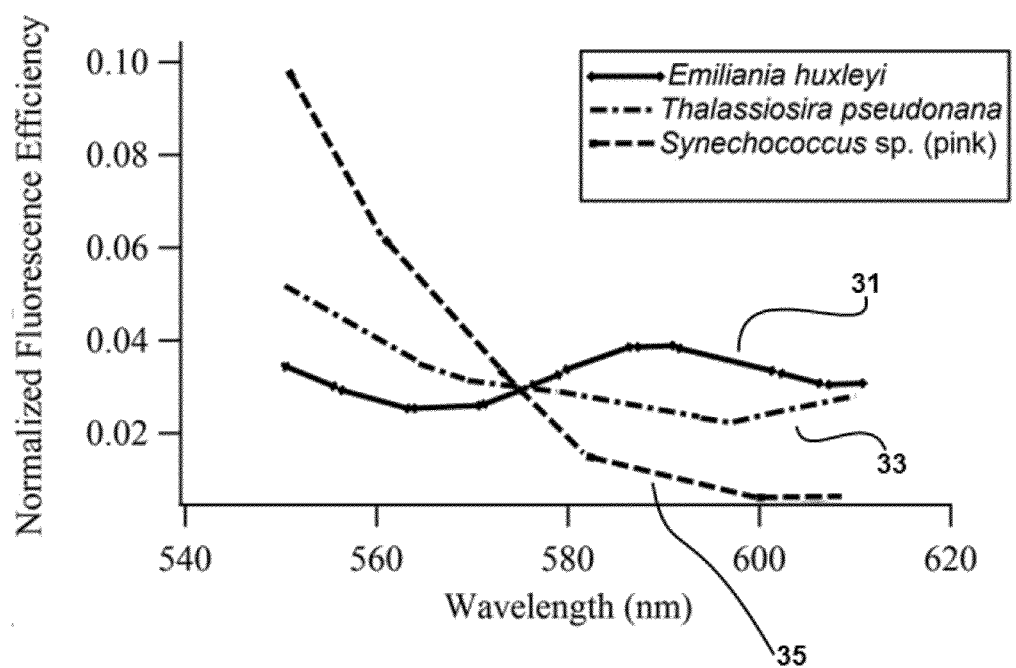
FIG. 3 is a graph of fluorescence excitation spectra of three phytoplankton species measured with a single cell spectralfluorometer.
Figure 4:
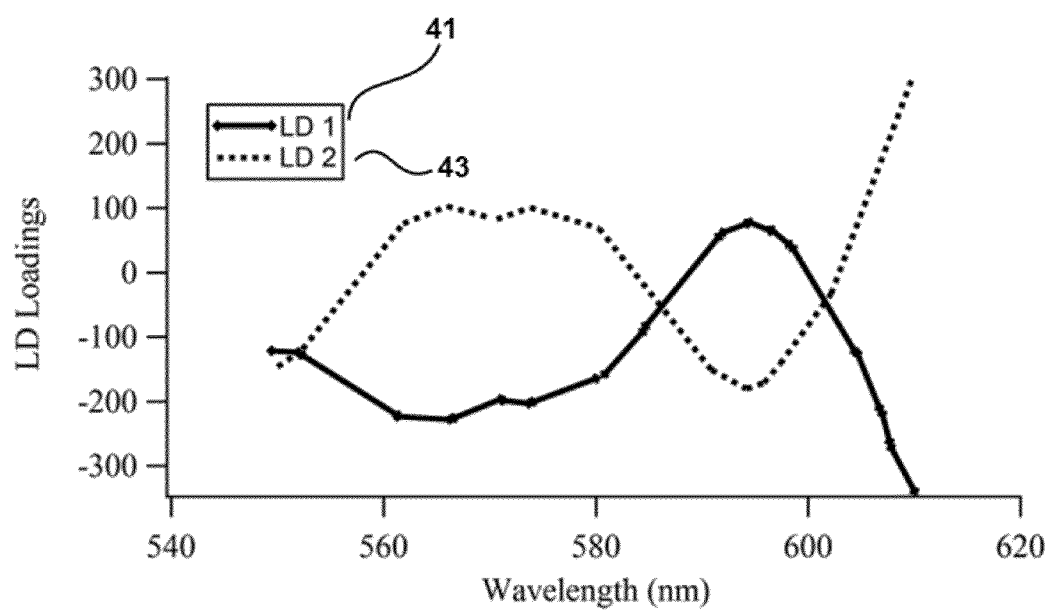
FIG. 4 shows the spectra of FIG. 3 separated using LDA via two functions.
Figure 5:
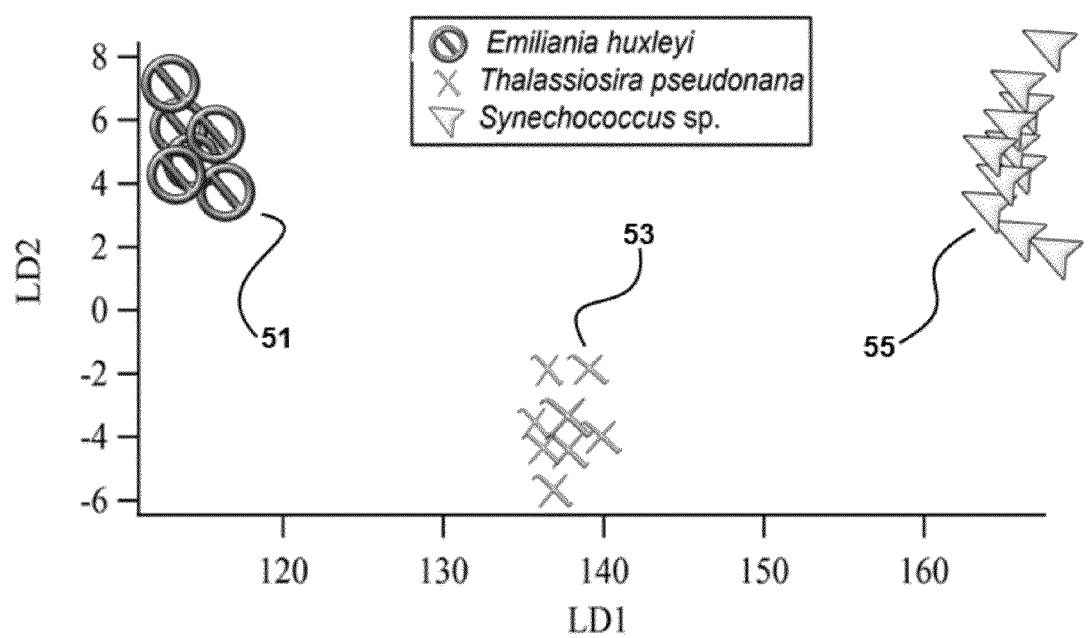
FIG. 5 illustrates classifying the phytoplankton species of FIG. 3, via the LDA functions illustrated in FIG. 4.

As discussed above, MOC may be applied to classification issues by designing MOEs whose spectra represent alternate discriminant vectors. These MOEs are designed to mimic the performance of the conventional linear discriminants. Referring now to FIG. 3, fluorescence excitation spectra 31, 33 and 35 of three phytoplankton species measured with a single cell spectral-fluorometer appear similar and overlapping. However, referring to FIG. 4, the spectra can be separated using LDA via two functions 41 (LDA 1) and 43 (LDA 2). That is, the scalar (or dot) product of the spectra in FIG. 3 with the vectors shown in FIG. 4 provides a set of discriminant scores that is distinct to each species of phytoplankton. FIG. 5 illustrates classifying the species, via LDA using the functions illustrated in FIG. 4.

Figure 6:
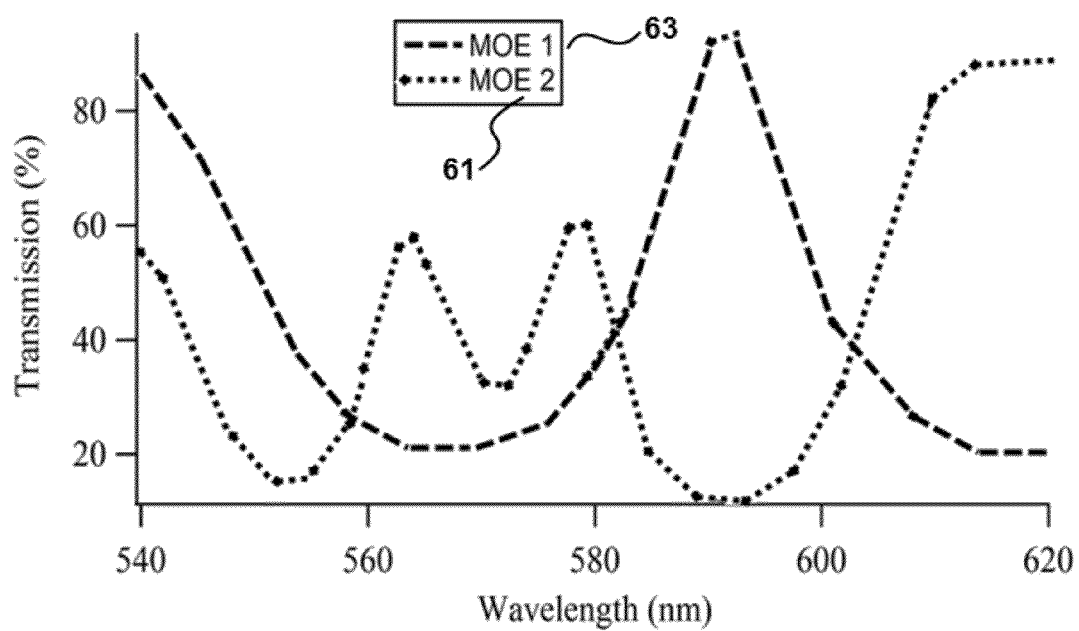
FIG. 6 is a dot product graph of MOE discriminant factors.
Figure 7:
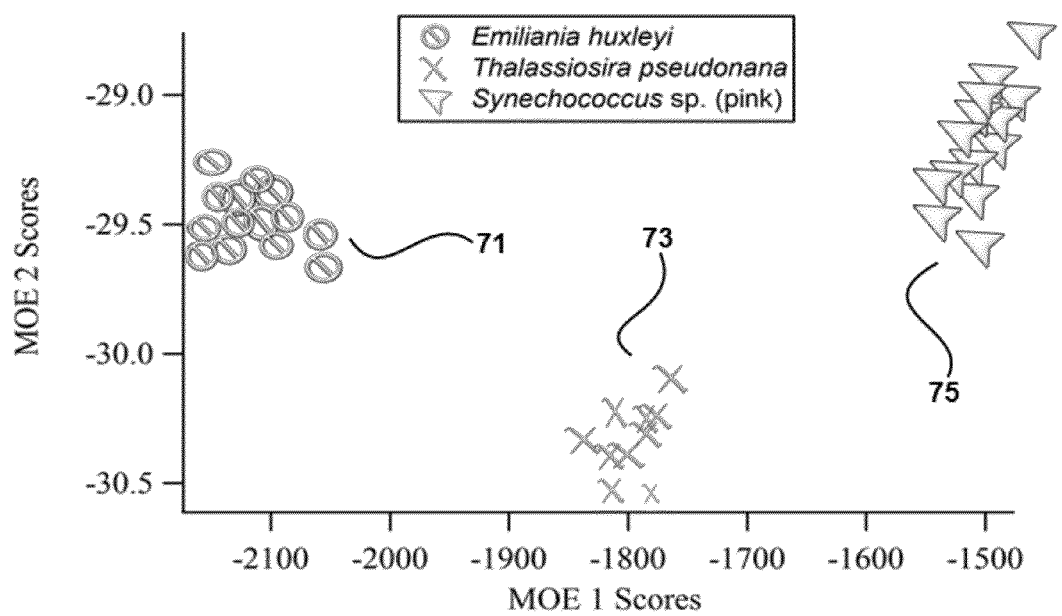
FIG. 7 illustrates classifying phytoplankton species using the MOE discriminant factors.

MOC may be applied to the same problem by designing two MOEs (transmission spectra shown in FIG. 6) whose spectra represent alternate discriminant vectors. These MOEs are designed to mimic the performance of the conventional linear discriminants in the FIG. 5. Referring to FIG. 6, dot products of these MOE spectral vectors with plankton spectra may be obtained mathematically from spectra or—more importantly—by exciting the plankton with a white light source filtered through the MOEs and measuring their total fluorescence. Thus the intensity of light emitted by the plankton becomes equivalent to a "score" on the MOE discriminant factor and is also used for classification analysis. See FIGS. 6 and 7 showing species 71, 73 and 75.

While conventional LDA requires a spectrometer and is slow, a camera can view the phytoplankton when they are excited through an MOE and "see" their score as their brightness. A series of such MOEs in a spinning filter wheel 21 makes it possible to measure scores on multiple discriminant factors quickly. Information on phytoplankton size may be acquired by using microscopic imaging in a "streak camera" mode, integrating a flowing sample volume until sufficient phytoplankton are accumulated to justify reading a camera frame. These may provide sufficient morphological and spectral analysis for classification.

Figure 8:
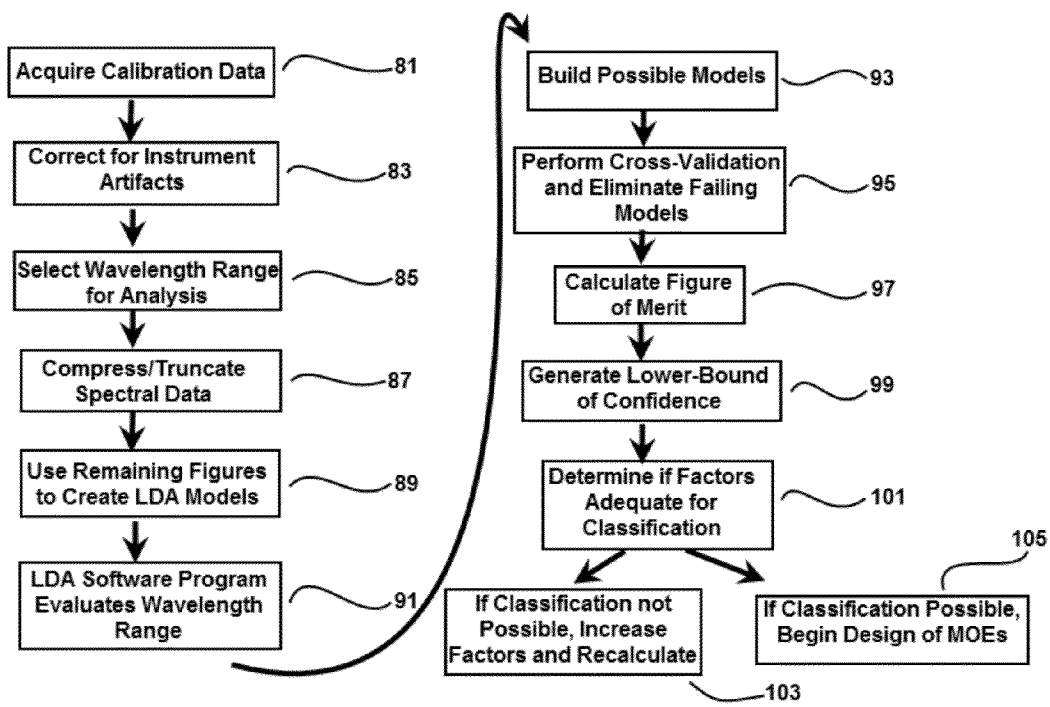
FIG. 8 is a flow chart representation of a method of designing MOEs.

In one embodiment of the present disclosure, a method is presented as shown in FIG. 8 for designing MOEs. Calibration data, at step 81, such as that shown in FIG. 3, is acquired for individual phytoplankton cells and analyzed using LDA. The calibration data is obtained for excitation wavelengths covering the accessible visible and UV wavelength regions—typically over the range of 350-650 nm inclusive (e.g. 360 nm, 380 nm, 400 nm, 420 nm, 440 nm, 460 nm, 480 nm, 500 nm, 520 nm, 540 nm, 560 nm, 580 nm, 600 nm, 620 nm, 640 nm or values between these values such as 355, 410, 555, etc.). Prior to analysis, at step 83, the spectra may be corrected for instrument artifacts to give as nearly "pure" spectral data as possible. A wavelength range is then selected for analysis at step 85. LDA begins by compressing the spectral data in the wavelength region of interest using a principal components analysis to reduce covariance at step 87. A principal components analysis is a mathematical procedure that uses an orthogonal transformation to convert a set of observations of possibly correlated variables into a set of values of uncorrelated variables called principal components. The number of principal components is less than or equal to the number of original variables. This transformation is defined in such a way that the first principal component has as high a variance as possible (that is, accounts for as much of the variability in the data as possible), and each succeeding component in turn has the highest variance possible under the constraint that it be orthogonal to (uncorrelated with) the preceding components. Principal components are guaranteed to be independent only if the data set is jointly normally distributed. PCA is sensitive to the relative scaling of the original variables.

The compressed data are truncated, also at step 87, to eliminate minor variables containing primarily noise while retaining the important spectral signatures. Truncation is done automatically by detecting a break in the slope of a log-eigenvalue plot that corresponds to the noise floor in the data. The remaining usable factors (for example, 10-30, but this may vary depending on the data set as known to those skilled in the art) are used for LDA at step 89. Each of these factors consists of linear combinations of the original wavelengths.

LDA models are created, at step 89, based on one or more of the remaining factors. For purposes of example only and not intended to be limiting, three-factor models, for purpose of example only and not intended to be limiting, can be generated using any permutation of three factors from the compressed data. Rather than use any form of simplifying approximation, a LDA software program goes through the calibration data by brute force: it evaluates every possible initial and final wavelength to define the wavelength range, at step 91, and it builds every possible model within each of those wavelength ranges, at step 93. This may be subject to the user input of how many factors it should be limited to. For all these models (typically many hundreds of thousands), a leave-one-out cross-validation is performed and models that fail to classify perfectly are eliminated at step 95, and then a figure of merit is calculated for all remaining models at step 97. A figure of merit is a quantity used to characterize the performance of a device, system or method, relative to its alternatives. Figures of merit may be defined for particular materials or devices in order to determine their relative utility for an application.

The figure of merit may be selected based on the quality of the least successful classification: the poorest Fisher ratio among all binary pairs of classes in the sample set. The Fisher ratio is a statistical test used when comparing statistical models that have been fit to a data set, in order to identify the model that best fits the population from which the data were sampled. Based on that poorest Fisher ratio, a lower-bound to the classification confidence may be generated, at step 99, and a decision may be made as to whether the number of factors is adequate to classify all the analytes, at step 101, for example phytoplankton, in the set. If not, the number of factors may be increased and the LDA calculation is repeated at step 103. The LDA program may also inform of which wavelength region is optimal for classification using a given number of discriminant factors, as well as providing the scores of each sample on those discriminant factors. At this point, design of the MOEs for the MOC system begins as indicated at step 105.

Combining information from images and optical spectra can be done in several ways. In the current disclosure, MOEs may be used to perform spectral discrimination. Thus, spectral and image analysis may be performed separately. In a further embodiment, several MOEs may be needed to mimic several linear discriminant functions covering a range of phytoplankton taxa.

Figure 9:
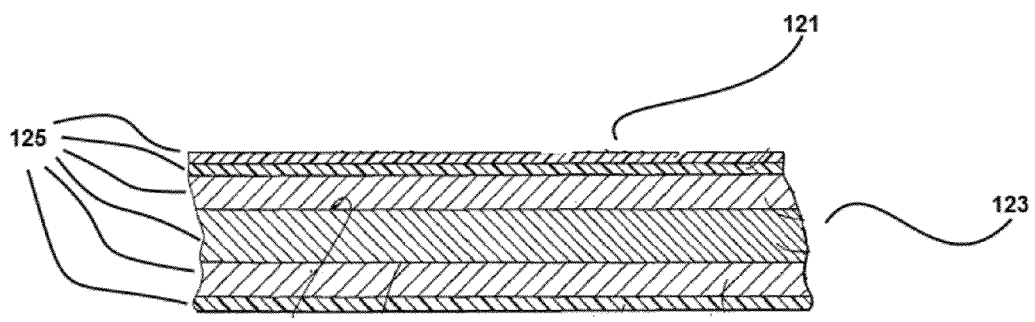
FIG. 9 is side view of one possible embodiment of an MOE.

As shown in FIG. 9, a MOE 121 is composed of a stack of thin films 123 which may give rise to a desired spectrum by interference effects. While the embodiment shown in FIG. 9 illustrates 6 layers, MOE 121 is not so limited and may have more or less layers. Design of MOE 121 may begin by defining a merit function and evaluating the function for a randomly-generated stack of thin films 123 for the set of calibration spectra limited to the optimal wavelength range determined by LDA. The layer thicknesses 125 are then varied to improve the merit function, and this process is repeated until the merit function no longer improves. This entire process may be repeated many thousands of times from many starting points to provide families of possible MOE 121 designs. In one embodiment, a cluster of computers may be tied together for processing needs as known to those skilled in the art. Each computer may run either a node algorithm or a master algorithm to aid in design.

For purposes of example only and not intended to be limiting, with respect to the phytoplankton shown in FIG. 3, the calibration set consisted of about 120 spectra covering an 80-nanometer wavelength range from 540-620 nm. MOEs were designed from silicon dioxide and niobium pentoxide, other compounds may be used to form the MOEs as known to those of skill in the art, including titanium dioxide, aluminum dioxide, etc. Further, MOEs could be made via holography or other methods known to those skilled in the art. Of these, 90+% had at least modest ability to reproduce the scores of the two discriminant functions from LDA analysis. More than 100 designs met every criterion applied: excellent fidelity to the LDA analysis, high sensitivity, compact structures and high throughput. Two candidate designs were selected for fabrication, each consisting of less than 11 thin films with a total thickness of less than 4 micrometers. However, this is provided for purposes of example only and various combinations of film number and thickness are available and the disclosure should not be understood to be limited to just the disclosed example.

Once a set of designs has been produced and restricted by all the criteria, the operator of the thin-film deposition system may select among them following an analysis that helps determine the tolerance of the designs to manufacturing errors. Once selected, substrates are cleaned and loaded into deposition chambers, designs are loaded into the control computers, and deposition begins. MOEs designed with respect to the species shown in FIG. 3 take approximately 4 days to fabricate. In that time, up to about 100 MOEs can be fabricated. After fabrication, MOEs must then be installed in an instrument to make measurements.

Linear discriminants are produced as a set for a particular classification. Likewise, MOEs 123 may be designed and fabricated to serve as a matched set. For purposes of example only, only two MOEs are required to distinguish the species *E. huxleyi* vs. *T. pseudonana* vs. *Synechococcus*. As the problem of discrimination gets more difficult, where species are more similarly-pigmented, there may be fewer designs possible and the manufacturing difficultly may increase. Using calibration instrument and conventional LDA, the present disclosure exceeds the capability of commercially-available fixed-wavelength spectral fluorometers that cannot discriminate between algal groups as similarly pigmented as a haptophyte (*E. huxleyi*) and a diatom (*T. pseudonana*).

In a further embodiment, conventional classification analysis is converted to a pseudo-quantitation problem. For purposes of example only, a method such as LDA, or a similar method as known to those skilled in the art, may be used to find canonical variates (CVs) or discriminant factors, which are patterns or vectors that best differentiate classes in a sample set. The "scores" of each sample on a given canonical value can then be used as targets for quantitation MOEs. The MOEs may be designed, for purposes of example only and not intended to be limiting, to "predict" what the scores of the sample will be on that CV.

MOEs 123, in one embodiment, may be designed using fluorescence excitation calibration spectra of individual plankton from cultures to separate different types of plankton from one another. In another embodiment, wild sources of plankton may be employed.

In a particular embodiment, a set of MOEs that may mimic the performance of the best linear discriminants is arranged on a filter wheel, chopper wheel 21, see FIG. 2, or similar apparatus as known to those skilled in the art, and plankton are sequentially excited through the MOEs using a light source—the spectral intensities of the light source is included in the design process of the MOEs as discussed above. As plankton pass through a viewing area, their fluorescence intensities under excitation by each MOE are recorded on a CCD camera, or other device as known to those skilled in the art, as a modulated "streak" or other similar device and analyzed to determine the classification of the plankton. This "streak camera" approach may make it possible to include some size information, for example streak profiles, in classification analysis.

Figure 10:
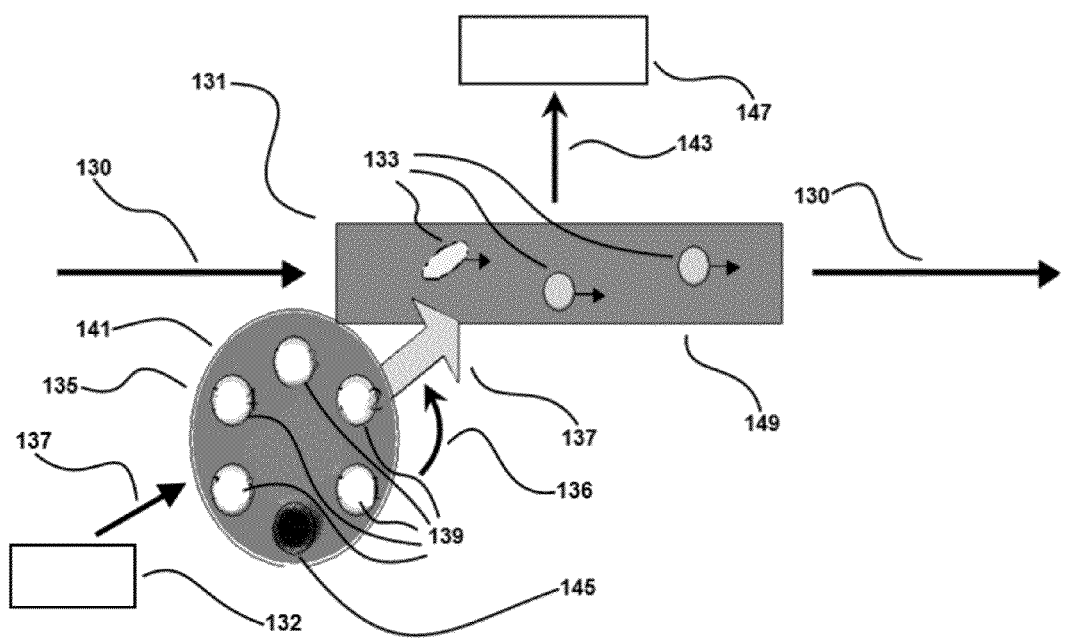
FIG. 10 is one embodiment of an imaging system.

Referring now to FIG. 10, one embodiment of an imaging system 131 is illustrated. Cells 133 flow 130 past optics 135 and are excited by broadband light 137, or any other suitable light as known to those skilled in the art, that passes through a series of MOEs 139 placed on a chopper 141. Chopper 141 modulates fluorescence excitation 143 by passing MOEs 139 into the beam of broadband light 137, for instance by rotating chopper 141 in the direction shown by arrow 136, but this may include other ways of interspersing the MOEs into the beam as known to those of skill in the art, provided by illumination device 132. For instance the rate may be 1 kHz or other rates known to those skilled in the art with the lower and upper limits being set by acceptable signal-to-noise required to distinguish signals from different particles.

For purposes of example only, assuming a residence time for a given phytoplankton cell in the field of view is 10 milliseconds, then 10 different excitation events may occur during phytoplankton transit. One of the excitation conditions will be a "full open" window 145, indicated in FIG. 10 by a darkened circle. Fluorescence excitation will be greatest when this window is open to the broad spectrum source, producing a maximum in the streak of fluorescence captured each time this open position occurs, see FIG. 11. This serves the role of a necessary blank measurement for IMOC, and also serves as a "timing mark" from which the fluorescence excitation sequence can be read directly from the image.

Figure 11:
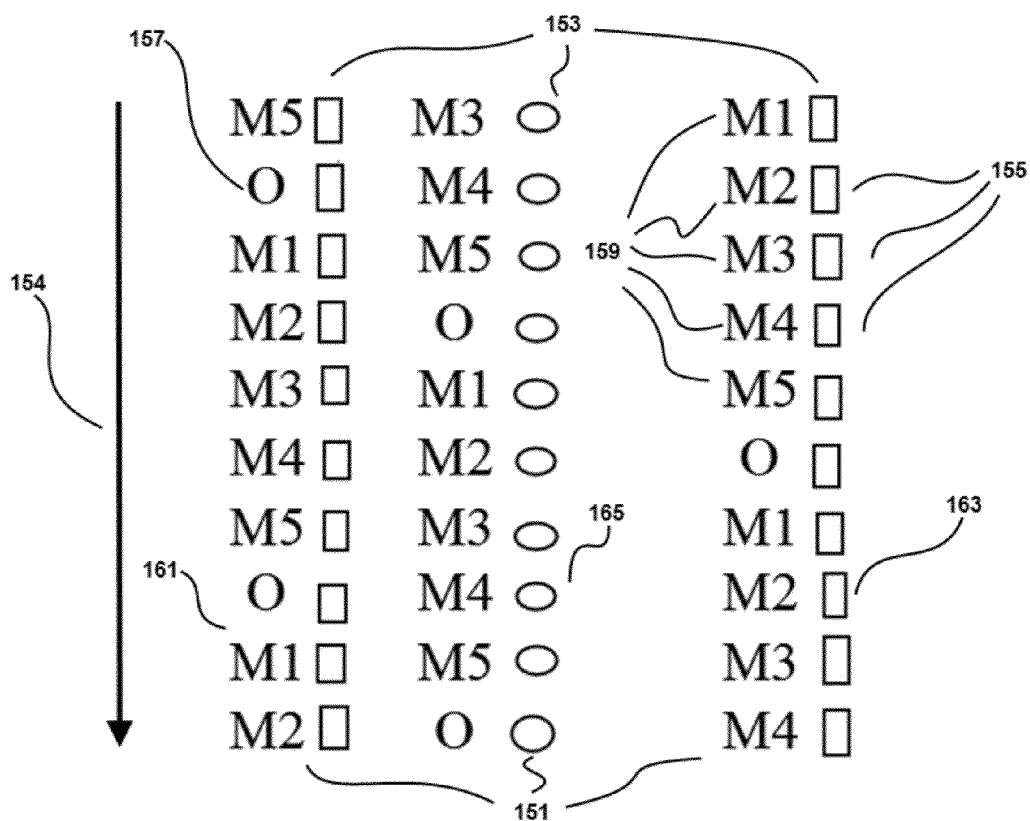
FIG. 11 shows one possible embodiment of streaks captured using the system of FIG. 10.

A single phytoplankton cell 133 will appear as a modulated streak of light in the image, see FIG. 11, with maxima in the streak serving as "timing marks" and the pulses that follow it being associated with analysis by different discriminant functions. The score of the phytoplankton fluorescence on each of these functions will serve to discriminate it from other organisms for which we are calibrated. In effect, each phytoplankton cell will be identified by something like in appearance to a "bar code" that is the result of its discriminant analysis. The width of the streak may provide a direct measure of size. In another embodiment, the raw intensity of signal is a distinct type of information available in the measurement.

Referring back to FIG. 10, camera 147, which may be an intensified 2048×512 pixel CCD camera, may be oriented with the short axis in the direction of fluid flow 130. For purposes of example only, camera 147 may image a region of sample approximately 2.5 mm in width and 625 micrometers in length, but other measurements are contemplated as known to those skilled in the art. Camera 147 may integrate until a predetermined amount of phytoplankton streaks accumulate in each frame to prevent overlap. For example, until no more than 50 small phytoplankton streaks accumulate in each frame. Assuming a concentration of $10^5$ cells/mL during a bloom, 50 phytoplankton would occupy ~500 nL, or about three sample cell 149 volumes per frame. If the sample flow rate 130 is set such that 10 frames per second are acquired, this equals a sampling rate of 5 µL/sec or about 0.3 mL/min. The average residence time of a phytoplankton 133 in sample cell 149 under these conditions would then be about 33 milliseconds. With video rate imaging, the sampled volume may reach 1 mL/minute and $10^5$ phytoplankton/sec with residence times of about 10 milliseconds. The upper limit to sampling rate is set by the minimum length of transit for a phytoplankton 133 through the sample cell 149 that would assure acquiring a complete bar code.

In one embodiment, as illustrated by FIG. 11, streak images 151 may be interpreted for use. For purposes of example only and not intended to be limiting, in one instance particles of plankton 133 that fluoresce are flowing and imaged onto the columns of a camera 147, for instance a CCD array camera. As FIG. 11 illustrates, tracks 153 of three phytoplankton cells, 133 in FIG. 10, are formed in the direction of flow 154. Open positions 145 in the chopper 141 appear as pulses 155 labeled with designation O 157. Designates 159 (M1-M5) refer to the MOE filters 139 installed in chopper 141. Referring to FIG. 11, the left streak 161 and right streak 163 represent the same species of phytoplankton entering the view at different moments. The central streak 165 is a larger cell 133 that differs in its discriminant analysis. In a further embodiment, the streaks generated, in addition to providing zones in which the particles are illuminated by each MOE in turn, may have a width that is related to the particle size and may be used as an additional element of information about the particle.

A typical algorithm for the interpretation may begin by calculating the standard deviation of the signal along each of the columns of the camera data. Standard deviations are typically only large when there is a large signal and also when there is adequate chopping of that signal as the particles flow "up" the image. The standard deviation may be used as the first step in recognizing the regions of the image that have fluorescence particles in them. After selecting these potential regions, that average signal along each column may be calculated and the ratio of standard deviation to signal in the center of each "particle region" may be computed. For a fully chopped signal, the ratio of the standard deviation to signal is relatively large and may be on the order of unity. In one instance, a ratio of about 0.6 is one dividing line between the particle tracks that are well-chopped to the observer's eye and those that are too out of focus to have been chopped well. Tracks with a lower ration than 0.6 may be discarded or deleted.

For the remaining tracks, the intensity integrated across each row of the vertical track may be used to identify the chopping sequences and on and off positions for each zone of selection may be selected. For each zone, a further refinement may be to look at the sums of the intensities in the columns, restricting the analysis to the zone of the track plus, for purposes of example only and not intended to be limiting, 15 pixels to either side. The resulting peaks represent the fluorescence signal for each illumination zone. From these peaks, analysis of the intensity and width of the streaks can be performed. The width may be analyzed in several ways. In one example, the width as a function of the fractional height of the peak is extracted as an array. These arrays are treated by principal components regression to provide an estimate of the particle size even when it is not in perfect focus.

In a still further embodiment, the filter wheel or chopper 141 may be designed to have one blocked region, not shown, leading to a clear dark space along the track. This position is identified and used to label the illumination zones associated with each filter of the filter wheel. The integrated intensity in these labeled zones are used to interpret the properties of the particles.

Figure 12:
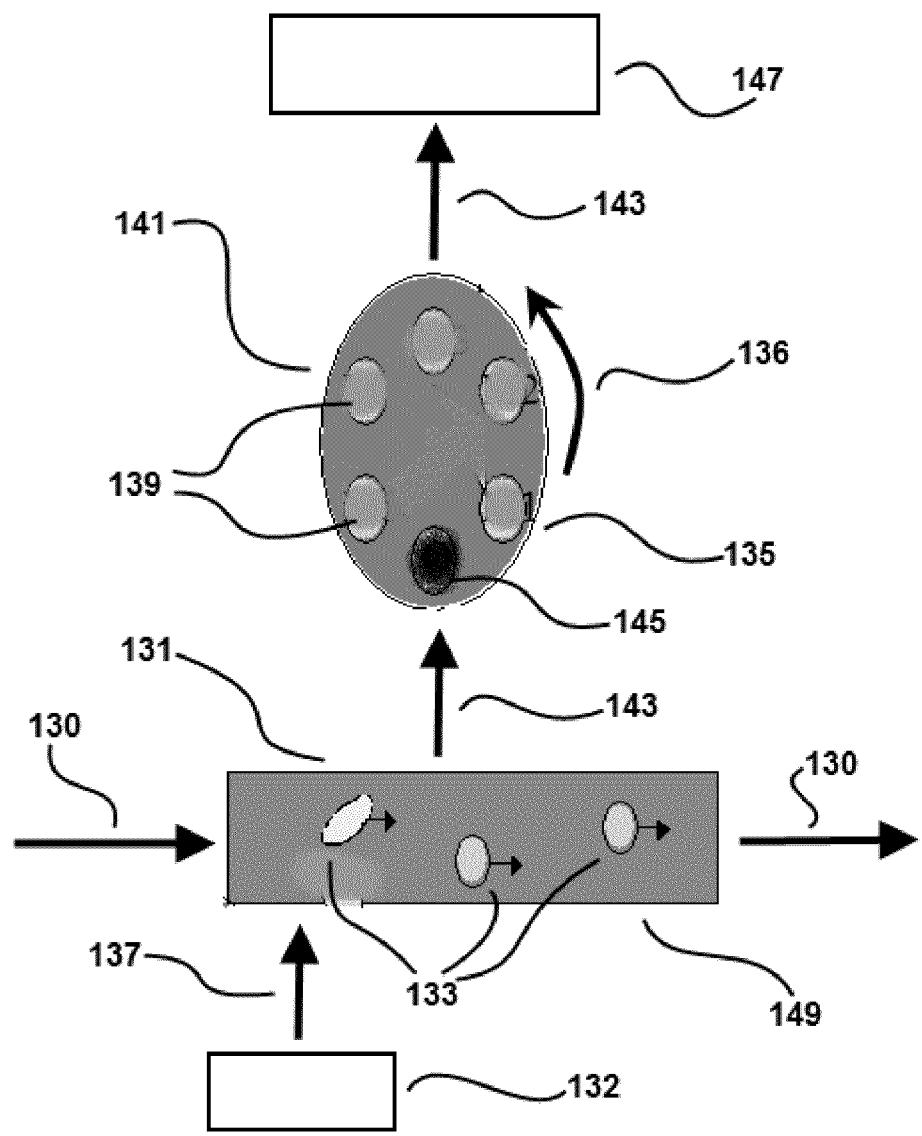
FIG. 12 shows an alternate embodiment of an imaging system.

In another embodiment, as shown by FIG. 12, for particles whose fluorescence emission is distinctive, the MOE-filter wheel 141 may not filter the light source 137 but would filter the emitted light 143 after being reflected and collected from the cells 133 and before reaching the camera 147. In a still further embodiment, for particles in which the reflectance or transmittance spectrum is distinctive, the MOE-filter wheel may be placed in either location, either before light strikes the sample or after it is reflected.

Figure 13:
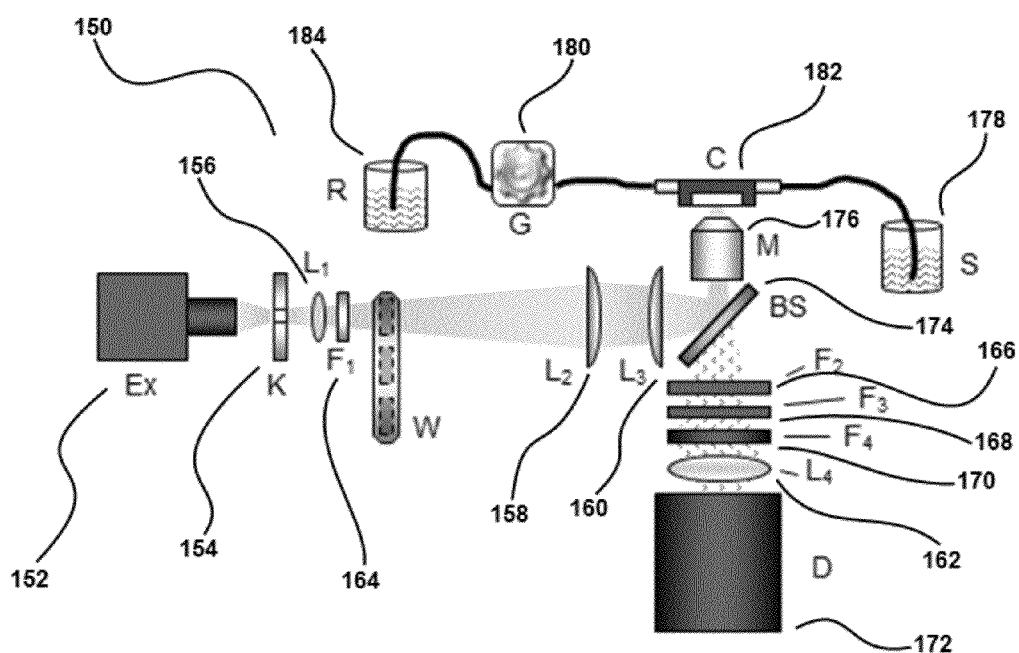
FIG. 13 shows an additional embodiment of an imaging system for use with the disclosure.

FIG. 13 illustrates another embodiment of the imaging system. Imaging system 150 contains an excitation source 152 and an aperture 154. For purpose of example only, four lenses, 156, 158, 160 and 162 are shown but the disclosure is not so limited as more or less lenses may be employed. Four filters, 164, 166, 168 and 170 may also be employed, the number of filters is also not limited by the disclosure as more or less lenses may be employed. These filters control the wavelength(s) of light presented to the sample and to the detector. A detector 172 is also included, which may be an array detector such as a CCD. A dichroic beam splitter 174 may also be provided. A microscope 176 may also be part the imaging system with the objective being varied, for purposes of example only, one suitable objective being 60×. Samples may also be subjected to multiple different objectives, either separately or simultaneously. A sample being analyzed is shown at 178. A gear pump 180 may also be employed to draw the sample 178 at various rates/types of flows including but not limited to pulsated flows, including low pulsation flows. However, other flow rates/types may be utilized including steady flow which may be at a high or low flow rate. A flow cell 182 may be used to bring sample 178 into view of the objective of microscope 176. A waste reservoir 184 may also be employed to hold samples once analysis has occurred or to contain waste products.

In a further embodiment, a form of registry is used to help identify which streaks correspond to which MOEs. Registry may be accomplished via timing marks, for example a blocked or open position on the filter wheel, in each streak. In an alternative embodiment, the system may be triggered to begin recording when particles enter the field of view. However, registry may be accomplished via numerous methods as known to those of skill in the art.

Measurements using a camera 147, such as a CCD or similar device, may require that device sensitivity be corrected or compensated or maintained so that sensitivity is independent of the spatial position of the particle in the image. This may require various background subtractions and flat-fielding routines be applied, such methods being known to those of skill in the art of imaging.

Flow rates for particles moving through the imaging area need to be fast enough that when the particles are in focus, the regions in which they are illuminated by each MOE are distinguishable. This may be accomplished by ensuring that the MOEs 139 positioned in the chopper wheel 141 have sufficient dark regions between them so that light is at least partially, if not completely, extinguished during some time between illuminations by different MOEs. Further, it is also preferred that the particles have moved a sufficient space in the image during this time interval so that there are regions between each illuminated zone that are "dark." In a further embodiment, some amount of overlap may be acceptable if the data is not compromised by the need to deconvolute neighboring "bright" zones without sufficient dark regions between them.

Flow rate may be determined by the slowest rate that permits observation of each illumination zone. For purposes of example only and not intended to be limiting, higher flow rates may result in lower signals. Further, too high of a flow rate 130 and the chopper wheel 141 does not rotate fully during transit. In one embodiment, the flow rate 130 and the chopper 141 rate may increase in speed. This may result in decreasing signals but maintaining observable streaks. In other embodiments, flow rate 130 and chopper 141 rate may vary with respect to one another and are not directly correlated to one another.

In one example of analysis of phytoplankton pigments, aliquots of 80 to 200 ml may be filtered onto 25 mm GF/F glass fiber filters using a gentle vacuum (<20 kPa) and then immediately frozen at −80° C. Samples will be first lyophilized at −50° C. followed by pigment extraction using 90% acetone at −20° C. for 24 h. To remove residual particles, extracts will be filtered through a 0.45 μm Teflon filter (Gelman Acrodisc) and transferred to amber glass vials. Ammonium acetate (1 mol L−1) will be added as an ion pairing agent in a ratio of 3 parts extract:1 part ammonium acetate to increase peak sharpness. Extracts will then be injected into a Shimadzu HPLC (LC10-AT) equipped with both a single monomeric and a polymeric reverse-phase C18 column in series. A non-linear binary gradient will be used for pigment separations (Pinckney et al. 1996). Solvent A consisted of 80% methanol: 20% ammonium acetate (0.5 mol L−1) and solvent B was 80% methanol: 20% acetone. Each sample will receive 20 μL of the synthetic carotenoid β-apo-8'-carotenal (Sigma-Aldrich Chemical Company, No. 10810) that serves as an internal standard. Absorption spectra and chromatograms (440 nm) will be acquired using a Shimadzu SPD-M10av photodiode array detector. Pigment peaks were identified by comparing retention times and absorption spectra to certified pigment standards (DHI, Denmark).

The contribution of individual algal groups to overall community composition may be determined using ChemTax (CHEMical TAXonomy), a matrix factorization program (Mackey et al. 1996; Wright et al. 1996). The program uses steepest descent algorithms to determine the best fit based on an initial estimate of pigment ratios for algal classes. The absolute contribution of any algal group is the concentration of total chl a (in μg L−1) contributed by that group. Relative contributions may be calculated as the proportion of total chl a accounted for by the group so that the sum of contributions from all groups equals one. Validated initial pigment ratio files will be taken from Mackey et al. (1996). Full discussions, validation, and sensitivity analyses for the ChemTax approach are found in Mackey et al. (1996), Wright et al. (1996), and Schluter et al. (2000).

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of in situ detection and classification of an analyte within a fluid sample, the method comprising:
   continuously flowing the fluid sample through a multivariate optical computing device, wherein the multivariate optical computing device illuminates an area of the fluid sample as it flows through the multivariate optical computing device to elicit a continuous series of spectral responses, and wherein a multivariate spectral response is formed by illuminating the analyte with a beam of light to excite the electrons in molecules of the analyte causing them to emit light of a lower energy;
   continuously measuring the series of the multivariate spectral responses as the fluid sample flows through the multivariate optical computing device;
   detecting an analyte in the sample based on an multivariate spectral response of the plurality of spectral responses; and classifying the analyte based on the multivariate spectral response generated by the analyte.

2. The method as in claim 1, wherein the analyte comprises a phytoplankton.

3. The method as in claim 1, wherein continuously measuring the series of multivariate spectral responses as the fluid sample flows through the multivariate optical computing device comprises:

continuously recording the series of multivariate spectral responses as the fluid sample flows through the multivariate optical computing device, wherein each multivariate spectral response is formed from a combination of a plurality of excitation spectra, each filtered by a multivariate optical element having a different transmission curve.

4. The method as in claim 1, wherein the beam of light is filtered prior to exciting the electrons in molecules of the analyte.

5. The method as in claim 4, wherein the beam of light passes through at least two multivariate optical elements to excite the electrons in molecules of the analyte, and wherein the spectra response formed by excitation of each filter is combined to form the multivariate spectral response.

6. The method as in claim 5, wherein each filter has a multi-wavelength spectral transmission curve that is different than the other filter.

7. A method of in situ detection and classification of the species of phytoplankton within a water sample, the method comprising:

continuously flowing the water sample through a multivariate optical computing device, wherein the multivariate optical computing device illuminates an area of the sample as it flows through the multivariate optical computing device to elicit a continuous series of spectral responses, and wherein a multivariate spectral response is formed by illuminating the analyte with a beam of light to excite the electrons in molecules of the analyte causing them to emit light of a lower energy;

continuously measuring the series of the multivariate spectral responses as the sample flows through the multivariate optical computing device;

detecting an phytoplankton particle in the sample based on an individual spectral response of the plurality of spectral responses; and classifying the phytoplankton particle based on the single spectral response.

8. The method as in claim 7, wherein continuously measuring the series of multivariate spectral responses as the fluid sample flows through the multivariate optical computing device comprises:

continuously recording the series of multivariate spectral responses as the fluid sample flows through the multivariate optical computing device, wherein each multivariate spectral response is formed from a combination of a plurality of excitation spectra, each filtered by a multivariate optical element having a different transmission curve.

9. The method as in claim 7, wherein the multivariate spectral response is formed by illuminating the analyte with a beam of light to excite the electrons in molecules of the analyte causing them to emit light of a lower energy.

10. The method as in claim 7, wherein the beam of light passes through at least two multivariate optical elements to excite the electrons in molecules of the analyte, and wherein the spectra response formed by excitation of each filter is combined to form the multivariate spectral response.

11. The method as in claim 10, wherein each filter has a multi-wavelength spectral transmission curve that is different than the other filter.

12. The method as in claim 7, wherein the water sample is pumped from a natural body of water.

13. The method as in claim 12, wherein the natural body of water is an ocean.

\* \* \* \* \*